(12) United States Patent
Kim et al.

(10) Patent No.: US 8,026,235 B1
(45) Date of Patent: Sep. 27, 2011

(54) PYRIDYL BENZOXAZINE DERIVATIVES, PHARMACEUTICAL COMPOSITION COMPRISING THE SAME, AND USE THEREOF

(75) Inventors: Ji Duck Kim, Yongin-si (KR); Hong-Chul Yoon, Incheon (KR); In Woo Kim, Seongnam-si (KR); Min Jae Cho, Uijeongbu-si (KR); In Young Lee, Yongin-si (KR); Sang Ho Lee, Yongin-si (KR); Eun Kyung Park, Yongin-si (KR); Kwon Jo Lim, Seoul (KR); Sang Hyun Nam, Seoul (KR)

(73) Assignee: Daewoong Pharmaceutical Co., Ltd., Sungnam-Si (KR)

( * ) Notice: Subject to any disclaimer, the term of this patent is extended or adjusted under 35 U.S.C. 154(b) by 0 days.

(21) Appl. No.: 12/909,513

(22) Filed: Oct. 21, 2010

(30) Foreign Application Priority Data

Oct. 13, 2010 (KR) .......................... 10-210-0099910

(51) Int. Cl.
C07D 413/14 (2006.01)
A61K 31/538 (2006.01)
(52) U.S. Cl. ..................................... 514/230.5; 544/105
(58) Field of Classification Search .................. 544/105; 514/230.5
See application file for complete search history.

(56) References Cited

FOREIGN PATENT DOCUMENTS

| KR | 10-2004-0034804 | 4/2004 |
|---|---|---|
| WO | 02/08221 | 1/2002 |
| WO | 02/16317 | 2/2002 |
| WO | 02/072536 | 9/2002 |
| WO | 02/076946 | 10/2002 |
| WO | 02/090326 | 11/2002 |
| WO | 03/014064 | 2/2003 |
| WO | 03/022809 | 3/2003 |
| WO | 03/029199 | 4/2003 |
| WO | 03/055484 | 7/2003 |
| WO | 03/062209 | 7/2003 |
| WO | 03/068749 | 8/2003 |
| WO | 03/070247 | 8/2003 |
| WO | 03/080578 | 10/2003 |
| WO | 03/097586 | 11/2003 |
| WO | 03/099284 | 12/2003 |
| WO | 2004/002983 | 1/2004 |
| WO | 2004/014871 | 2/2004 |
| WO | 2004/033435 | 4/2004 |
| WO | 2004/035549 | 4/2004 |
| WO | 2004/055003 | 7/2004 |
| WO | 2004/055004 | 7/2004 |
| WO | 2005/002551 | 1/2005 |
| WO | 2005/007648 | 1/2005 |
| WO | 2005/016890 | 2/2005 |
| WO | 2005/047279 | 5/2005 |
| WO | 2006/006740 | 1/2006 |
| WO | 2006/006741 | 1/2006 |
| WO | 2006/063178 | 6/2006 |
| WO | 2006/124753 | 11/2006 |
| WO | 2007/067619 | 6/2007 |
| WO | 2007/067757 | 6/2007 |
| WO | 2007/073303 | 6/2007 |
| WO | 2007/090134 | 8/2007 |
| WO | 2008/006481 | 1/2008 |
| WO | 2008/007211 | 1/2008 |
| WO | 2008/018827 | 2/2008 |

OTHER PUBLICATIONS

Chalmers (TiPS vol. 17, pp. 166-172 Apr. 1996).*
Birder et al., "Vanilloid receptor expression suggests a sensory role for urinary bladder epithelial cells," *PNAS*, 98 (23): 13396-13401, 2001.
Buck et al., "The Neuropharmacology of Capsaicin: Review of Some Recent Observations," *Pharmacological Reviews*, 38(3): 179-226, 1986.
Caterina et al., "The capsaicin receptor: a heat-activated ion channel in the pain pathway," *Nature*, 389: 816-824, 1997.
Caterina et al., "Impaired Nociception and Pain Sensation in Mice Lacking the Capsaicin Receptor," *Science*, 288: 306-313, 2000.
Mezey et al., "Distribution of mRNA for vanilloid receptor subtype 1 (VR1), and VR1-like immunoreactivity, in the central nervous system of the rat and human," *PNAS*, 97 (7): 3655-3660, 2000.
Nozawa et al., "Distribution and characterization of vanilloid receptors in the rat stomach," *Neuroscience Letters*, 309: 33-36, 2001.
Premkumar et al., "Induction of vanilloid receptor channel activity by protein kinase C," *Nature*, 408: 985-990, 2000.
Szallasi et al., "Vanilloid Receptor TRPV1 Antagonists as the Next Generation of Painkillers. Are We Putting the Cart before the Horse?," *Journal of Medicinal Chemistry*, 47 (11): 2717-2723, 2004.
Tominaga et al., "The Cloned Capsaicin Receptor Integrates Multiple Pain-Producing Stimuli," *Neuron*, 21: 531-543, 1998.
Yiangou et al., "Vanilloid receptor 1 immunoreactivity in inflamed human bowel," *The Lancet*, 357: 1338-1339, 2001.

* cited by examiner

*Primary Examiner* — Kahsay T Habte
(74) *Attorney, Agent, or Firm* — Seed IP Law Group PLLC

(57) ABSTRACT

Discloses is a benzoxazine benzimidazole derivative, represented by Chemical Formula 1, functioning as an antagonist to the vanilloid receptor-1, a pharmaceutical composition comprising the same, and the use thereof. The benzoxazine benzimidazole derivative can be useful for preventing or treating a disease associated with antagonistic activity of vanilloid receptor-1, without hyperthermia:

[Chemical Formula 1]

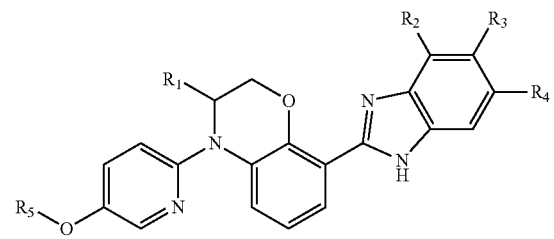

wherein, $R_1$, $R_2$, $R_3$, $R_4$ and $R_5$ are as defined in the specification.

13 Claims, No Drawings

PYRIDYL BENZOXAZINE DERIVATIVES, PHARMACEUTICAL COMPOSITION COMPRISING THE SAME, AND USE THEREOF

FIELD OF THE INVENTION

The present invention relates to a novel pyridyl benzoxazine derivative as an antagonist against a vanilloid receptor-1 without hyperthermia, a pharmaceutical composition comprising the same as an active ingredient, and a use thereof.

BACKGROUND OF THE INVENTION

A vanilloid receptor, a receptor for capsaicin (trans-8-methyl-N-vanillyl-6-nonenamide), has been cloned in 1997 and called vanilloid receptor subtype 1 (hereinafter referred to as "TRPV1") by Caterina et al. (Caterina et al., Nature, 389, 816 (1997)). Located on small unmyelinated nerve fibers (C-fibers) and also on large myelinated nerve fibers (A-fibers), TRPV1 is an ion channel which plays an important role in sensitizing pain stimuli by introducing a strong influx of cations such as calcium and sodium ions into the nerve endings upon activation in response to external or internal stimuli. External stimuli capable of activating TRPV1 are reported to include heat and acids as well as vanilloid compounds (Tominaga et al., Neuron, 21, 531 (1998)). The internal stimuli to TRPV1, on the other hand, are leukotriene metabolites such as 12-hydroperoxyeicosa tetraenoic acid (12-HPETE) (Hwang at al., PNAS, 97, 3655 (2000)), and arachidonic acid derivatives such as anandamide (Premkumar et al., Nature, 408, 985 (2000)).

On the basis of these physiological activities, TRPV1 has attracted intensive attention as an integral controller playing a pivotal role in transferring various external stimuli into nerve cells. According to a report, TRPV1 knock-out mice respond like normal mice to general stimuli, but showed greatly reduced pain response to heat or thermal hyperalgesia (Caterina et al., Science, 288, 306 (2000)).

TRPV1 is expressed mainly in primary sensory neurons (Caterina et al., Nature, 389, 816 (1997)), which are responsible for controlling the functions of the skin, bone, and internal organs such as the bladder, the gastrointestinal tract, the lungs, and so on. In addition, TRPV1 is also distributed in other neurons on the central nervous system, the kidney, the stomach, and T-cells (Nozawa et al., Neuroscience Letter, 2001, 309, 33; Yiangou et al., Lancet (North America Edition), 357, 1338 (2001); Birder et al., PNAS, 98, 13396 (2001)) and throughout the entire body, and plays important roles in cell division and cellular signal control.

Also, associated with the control mechanism of the activity of TRPV1 are acute pain, chronic pain, neuropathic pain, postoperative pain, migraines, arthralgia, neuropathy, neuronal damages, diabetic neuropathy, neurological disorders, neurodermatitis, stroke, bladder hypersensitivity, irritable bowel syndrome, respiratory disorders such as asthma, chronic obstructive pulmonary disease, irritation to the skin, eye, and mucous membranes, itching, fever, reflux esophagitis, gastric duodenal ulcer, inflammatory intestinal diseases, and urge incontinence (Korean Laid-Open Publication No. 2004-0034804), obesity (Pharmacol. Rev., 38, 179 (1986)), and glaucoma (WO07/090,134).

As compounds capable of modulating TRPV1 activity, agonists such as a capsaicin derivative (DA-5018) and resiniferatoxin are used as pain-relief drugs or are under clinical study (Szallasi, J. Med chem., 47, 2717 (2004)), while various TRPV1 antagonists including capsazepine and iodoresiniferatoxin are under pre-clinical studies (WO02/008221, WO03/062209, WO04/055003, WO04/055004, WO04/002983, WO02/016317, WO04/035549, WO04/014871, WO03/099284, WO03/022809, WO02/090326, WO02/072536, WO03/068749, WO04/033435, WO02/076946, WO03/055484, WO03/014064, WO03/080578, WO03/097586, WO03/070247, WO03/029199, WO05/002551, WO05/007648, WO05/016890, WO05/047279, WO06/006740, WO06/006741, WO06/063178, WO06/124753, WO06/063178, WO07/067,619, WO07/067,757, WO07/073,303, WO08/006,481, WO08/007,211, and WO08/018,827).

SUMMARY OF THE INVENTION

It is therefore an object of the present invention to provide a novel pyridyl benzoxazine derivative which shows inhibitory activity against a vanilloid receptor-1 (TRPV1) which does not have side effects on body temperature modulation.

It is another object of the present invention to provide a pharmaceutical composition comprising the pyridyl benzoxazine derivative as an active ingredient.

It is a further object of the present invention to provide a method for the treatment of disorders associated with the control mechanism of the activity of TRPV1 using the pyridyl benzoxazine derivative.

DETAILED DESCRIPTION OF THE INVENTION

In accordance with an aspect thereof, the present invention pertains to the compound represented by the following chemical formula 1 or its pharmaceutically acceptable salts.

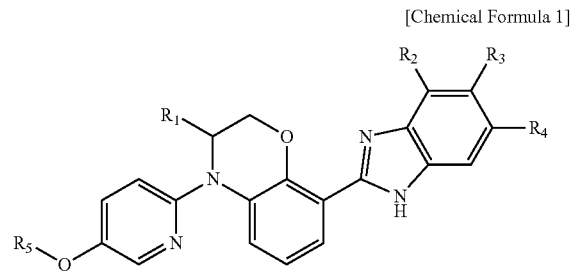

[Chemical Formula 1]

wherein,
$R_1$ is hydrogen or $C_{1-3}$ hydroxyalkyl;
$R_2$ is hydrogen or halogen;
$R_3$ is hydrogen or halogen; and
$R_4$ is hydrogen, halogen, $C_{1-4}$ alkyl, $C_{1-3}$ haloalkyl or $C_{1-3}$ haloalkoxy; and
$R_5$ is $C_{1-4}$ alkyl.

Preferably, $R_1$ is hydrogen or hydroxymethyl.
In a preferred embodiment, $R_2$ and $R_3$ are each hydrogen; $R_4$ is $C_{1-4}$ alkyl or $C_{1-3}$ haloalkoxy.
In another preferred embodiment, $R_2$ is hydrogen; $R_3$ and $R_4$ are each halogen.
In a further preferred embodiment, $R_2$ is halogen, $R_3$ is hydrogen, and $R_4$ is halogen, $C_{1-3}$ haloalkyl or $C_{1-3}$ haloalkoxy.
Also preferably, $R_2$ is hydrogen, Br or Cl.
In still a further preferred embodiment, $R_3$ is hydrogen, F or Cl.
In still another preferred embodiment, $R_4$ is Br, Cl, $C(CH_3)_3$, $CF_3$ or $OCF_3$.
In yet another preferred embodiment, $R_5$ is methyl.

Concrete examples of representative compounds of Chemical Formula 1 include:

1) 8-(6-tert-butyl-1H-benzo[d]imidazol-2-yl)-4-(5-methoxypyridin-2-yl)-3,4-dihydro-2H-benzo[b][1,4]oxazine,
2) (S)-(4-(5-methoxypyridin-2-yl)-8-(6-(trifluoromethyl)-1H-benzo[d]imidazol-2-yl)-3,4-dihydro-2H-benzo[b][1,4]oxazin-3-yl)methanol,
3) (S)-(8-(5,6-dichloro-1H-benzo[d]imidazol-2-yl)-4-(5-methoxypyridin-2-yl)-3,4-dihydro-2H-benzo[b][1,4]oxazin-3-yl)methanol,
4) (S)-(4-(5-methoxypyridin-2-yl)-8-(6-(trifluoromethoxy)-1H-benzo[d]imidazol-2-yl)-3,4-dihydro-2H-benzo[b][1,4]oxazin-3-yl)methanol,
5) (S)-(8-(4-bromo-6-(trifluoromethoxy)-1H-benzo[d]imidazol-2-yl)-4-(5-methoxypyridin-2-yl)-3,4-dihydro-2H-benzo[b][1,4]oxazin-3-yl)methanol,
6) (S)-(8-(6-chloro-5-fluoro-1H-benzo[d]imidazol-2-yl)-4-(5-methoxypyridin-2-yl)-3,4-dihydro-2H-benzo[b][1,4]oxazin-3-yl)methanol,
7) (S)-(8-(4-bromo-6-(trifluoromethyl)-1H-benzo[d]imidazol-2-yl)-4-(5-methoxypyridin-2-yl)-3,4-dihydro-2H-benzo[b][1,4]oxazin-3-yl)methanol,
8) (S)-(8-(4-chloro-6-(trifluoromethyl)-1H-benzo[d]imidazol-2-yl)-4-(5-methoxypyridin-2-yl)-3,4-dihydro-2H-benzo[b][1,4]oxazin-3-yl)methanol,
9) (S)-(8-(4,6-dibromo-1H-benzo[d]imidazol-2-yl)-4-(5-methoxypyridin-2-yl)-3,4-dihydro-2H-benzo[b][1,4]oxazin-3-yl)methanol.

Further, tautomerization of the compounds of formula 1 may be possible by the migration of hydrogen in the position No. 1 and 3 of formula 1, as follow.

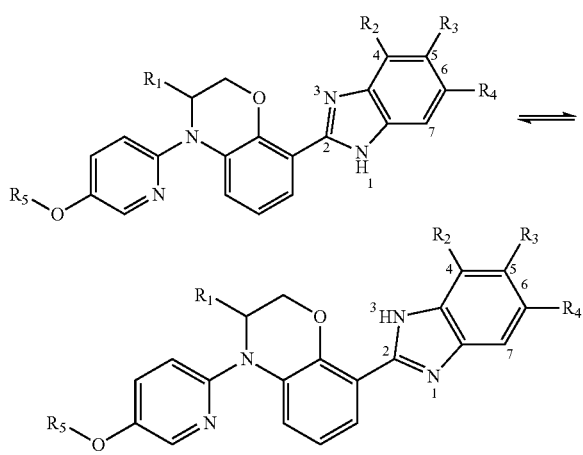

As shown above, the compounds of formula 1 may be in the form of salts, particularly pharmaceutically acceptable salts. The pharmaceutically available salts suitable for use in the present invention are those typically used in the art, such as acid addition salts, and include those disclosed in the literature (J. Pharm. Sci., 66, 1 (1977)). Examples of the pharmaceutically acceptable acid addition salts suitable for use in the present invention include salts of inorganic acids, such as hydrochloric acid, hydrobromic acid, phosphoric acid, orthophosphoric acid, sulfuric acid, and so on; and salts of organic acids, such as methanesulfonic acid, benzensulfonic acid, toluenesulfonic acid, acetic acid, propionic acid, lactic acid, citric acid, fumaric acid, malic acid, succinic acid, salicylic acid, maleic acid, glycerophosphoric acid, acetylsalicylic acid, and so on. In addition, pharmaceutically acceptable metal salts may be prepared using bases according to a conventional method. Alkali metal salts or alkaline earth metal salts, for example, may be obtained by dissolving compounds of formula 1 in an excess of an alkali metal hydroxide or alkaline earth metal hydroxide solution, filtering off non-dissolved compound salts, and vaporizing and drying the filtrate. In this regard, sodium, potassium or calcium salts are pharmaceutically suitable metal salts. In addition, silver salts corresponding to the metal salts can be obtained by reacting alkaline metal or alkali earth metal with suitable silver salts (e.g., nitrate).

The compounds of formula 1 of the present invention include a pharmaceutically acceptable salt as well as a solvate and hydrate preparable from them, and a stereoisomer. The solvate, hydrate and stereoisomer may be prepared from the compound of formula 1 according to a conventional method.

The compounds of formula 1 may be prepared in crystalline or non-crystalline forms. If crystalline, the compounds may be optionally hydrated or solvated. Compounds with various amounts of water as well as stoichiometric hydrates of formula 1 fall into the scope of the present invention. Solvates of formula 1 according to the present invention comprise both stoichiometric and non-stoichiometric solvates.

It is believed that, because they possess antagonistic activity against the vanilloid receptor-1, benzoxazine benzimidazol derivatives of formula 1 have potential to be used for the prevention and treatment of indications relevant thereto. Thus, the present invention also provides a pharmaceutical composition comprising the compound of formula 1, or the pharmaceutically acceptable salt, hydrate, solvate, or isomer thereof as an active ingredient, which is useful for the prevention and treatment of a disease associated with antagonistic activity of vanilloid receptor-1.

The present invention provides a method for preventing or treating indications for which antagonism to the vanilloid receptor-1 is helpful in the therapy thereof in a mammal, which comprises administering the compound of formula 1, or the pharmaceutically acceptable salt, hydrate, solvate or isomer thereof, to the mammal.

Further, the present invention provides a method for inhibiting a vanilloid receptor-1 in a mammal, which comprises administering the compound of formula 1, or the pharmaceutically acceptable salt, hydrate, solvate, or isomer thereof, to the mammal As used herein, the term "a disease associated with antagonistic activity of vanilloid receptor-1" refer to acute or chronic disease that require treatment to inhibit activity of vanilloid receptor-1 and exemplary disease include pain such as acute pain, chronic pain, neuropathic pain, postoperative pain; migraine, arthralgia; neuropathy; neuronal damages; diabetic neuropathy; neurological illness; neurodermatitis; stroke; bladder hypersensitivity; obesity; irritable bowel syndrome; respiratory disorders such as cough, asthma, and chronic obstructive pulmonary disease; glaucoma; burns; psoriasis; itching; vomiting; irritation of the skin, eyes, and mucous membranes; and inflammatory diseases such as reflux esophagitis, gastric duodenal ulcers, and inflammatory intestinal diseases.

The pharmaceutical composition of the present invention is generally formulated for oral or parenteral administration according to standard pharmaceutical practice. And these formulations may comprise the above active ingredients, in combination with an additive such as a pharmaceutically acceptable carrier, adjuvant, or diluent. Illustrative, but non-limitative examples of the carrier include physiological saline, polyethylene glycol, ethanol, vegetable oil, and isopropylmyristate. Illustrative, but non-limitative examples of the diluent include lactose, dextrose, sucrose, mannitol, sorbitol, cellulose, and/or glycin. For example, the compounds of formula 1, or the pharmaceutically acceptable salt, hydrate, solvate, or isomer thereof, may be dissolved in oils, propyleneglycol, or other solvents, which are usually used for the preparation of injections. For topical use, the compounds of the present invention, or the pharmaceutically acceptable salt, hydrate, solvate, or isomer thereof may be formulated into ointments or creams.

Below, a description will be given of formulation methods and excipients, but this description is not intended to limit the present invention.

Although the compounds of formula 1 of the present invention or a pharmaceutically acceptable salt, hydrate, solvate or isomer thereof, themselves are TRPV1 antagonists, the possibility is not excluded that modified forms thereof in an intracellular environment or metabolites thereof act as effective principles responsible for the medicinal activity.

Pharmaceutical dosage forms of the compounds of formula 1 according to the present invention include pharmaceutically acceptable salts or solvates of the compounds of the present invention alone or in combination with other pharmaceutically active compounds suitably bound or assembled thereto.

For the preparation of injections, the compounds of formula 1 according to the present invention or a pharmaceutically acceptable salt, hydrate, solvate or isomer may be dissolved, suspended or emulsified in an aqueous solvent such as physiological saline, 5% dextrose, etc., or a nonaqueous solvent, such as synthetic fatty acid glyceride, higher fatty acid esters, propylene glycol, etc. The formulation of the present invention may comprise conventional additives such as dissolving agents, isotonic agents, suspensions, emulsifying agents, stabilizer, and preservatives.

Depending on a patient's state and weight, severity of disease, dosage form, and administration route and period, the administration dose of the compounds of formula 1 according to the present invention or the pharmaceutically acceptable salt, hydrate, solvate, or isomer thereof, may be suitably selected by those skilled in the art. For effective therapy, the compounds of formula 1 according to the present invention or the pharmaceutically acceptable salt, hydrate, solvate, or isomer thereof are administered in a dose from 0.0001 to 100 mg/weight kg a day and preferably in a dose from 0.001 to 100 mg/weight kg a day. Administration may be conducted orally or parenterally once or many times in a partitioned manner in a day.

According to the administration method, the pharmaceutical composition may comprise the compound of formula 1 according to the present invention, or the pharmaceutically acceptable salt, hydrate, solvate, or isomer thereof in an amount from 0.001 to 99% by weight, and preferably in an amount from 0.01 to 60% by weight.

The pharmaceutical composition of the present invention may be administered via various routes to mammalians such as mice, rats, livestock, humans, etc. All administration types may be expected, including, for example, an oral administration, a rectal administration, or an intravenous, intramuscular, subcutaneous, intra-endometrial or intracerbroventricular injection.

In accordance with another aspect thereof, the present invention provides a method for preparing the compound of Chemical Formula 1, as illustrated in the following Reaction Scheme 1 or 2.

The following reaction scheme 1 is used to synthesize the compounds represented by Chemical Formula 1 wherein $R_1$ is hydrogen (Compound 1a).

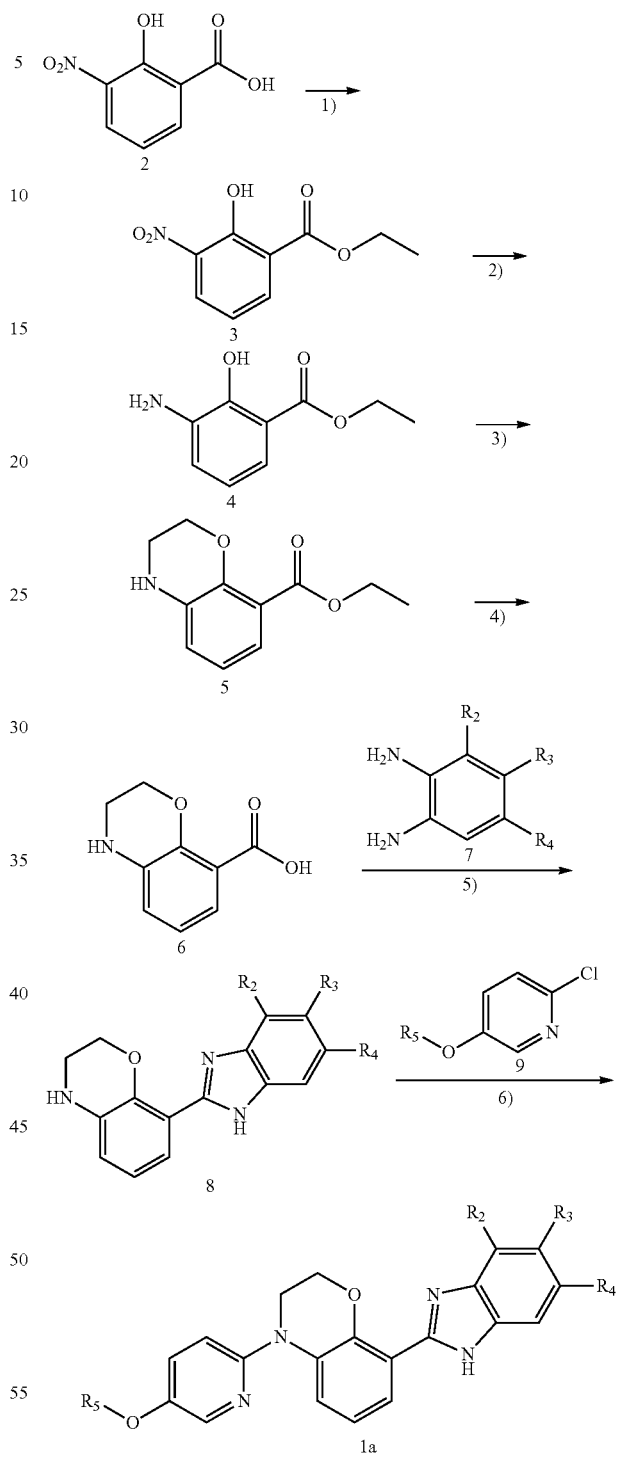

wherein, $R_2$, $R_3$, $R_4$ and $R_5$ are respectively as defined above.

In step 1), as seen in Reaction Scheme 1, compound 2 is allowed to react in an organic solvent in the presence of HCl to afford compound 3. In this step, the organic solvent may be methanol or ethanol and the reaction may be conducted for 16 to 24 hrs with heating under reflux.

In step 2), compound 3 is reduced into compound 4 in the presence of the Pd/C catalyst in an organic solvent in a hydrogen reactor. This reduction reaction may be conducted at room temperature for 2 to 5 hrs in methanol or ethanol as the solvent while the catalyst may be used in an amount of 5 to 10 wt % based on the total weight of compound 3.

In step 3), compound 4 is reacted with dibromoethane under basic conditions to yield compound 5. For this reaction, dibromoethane may be used in an amount of 1.1 to 1.2 moles per mole of compound 4 in the presence of $K_2CO_3$ as a base. This reaction may be carried out for 2 to 3 hrs with heating under reflux.

In step 4), compound 5 is hydrolyzed into compound 6 in the presence of lithium hydroxide monohydrate. In this regard, this hydrolysis may be conducted at room temperature for 6 to 8 hrs with the use of 2 to 3 moles of lithium hydroxide monohydrate per mole of compound 5.

In step 5), compound 6 is condensed with compound 7 and O-(7-azabenzotriazol-1-yl)-N,N,N',N'-tetramethyluronium hexafluorophosphate in a solvent under basic conditions to yield an amide compound, followed by cyclization into compound 8 in the presence of acetic acid without purification. Compound 7 may be synthesized using a typical method or a commercial variant may be used. It is used in an amount of 1 mole per mole of compound 6. Diisopropylamine is useful as a base while dimethylformamide may serve as the solvent. The condensation may be carried out at room temperature for 16 to 24 hrs and the cyclization at 70~75° C. for 2 to 4 hrs.

Turning to step 6), compound 8 is reacted with compound 9 in the presence of a catalyst and a ligand in an organic solvent under basic conditions to synthesize compound 1a. Compound 9 may be obtained by chemical synthesis or may be purchased. It is used in an amount of 1 mole per mole of compound 8. For use in this reaction, $Pd(OAc)_2$ may be properly suggested as the catalyst, 2,2'-bis(diphenylphosphino)-1,1'-binaphthyl as the ligand, $Cs_2CO_3$ as the base and toluene or 1,4-dioxane as the organic solvent. This reaction may be conducted at 90 to 110° C. for 12 to 18 hrs (Mark M. Hooper et. al., Journal of Organic Chemistry, 68, 2861 (2003)).

The following reaction scheme 2 accounts for the synthesis of the compounds represented by Chemical Formula 1 wherein $R_1$ is $C_{1-3}$ hydroxyalkyl (Compound 1b).

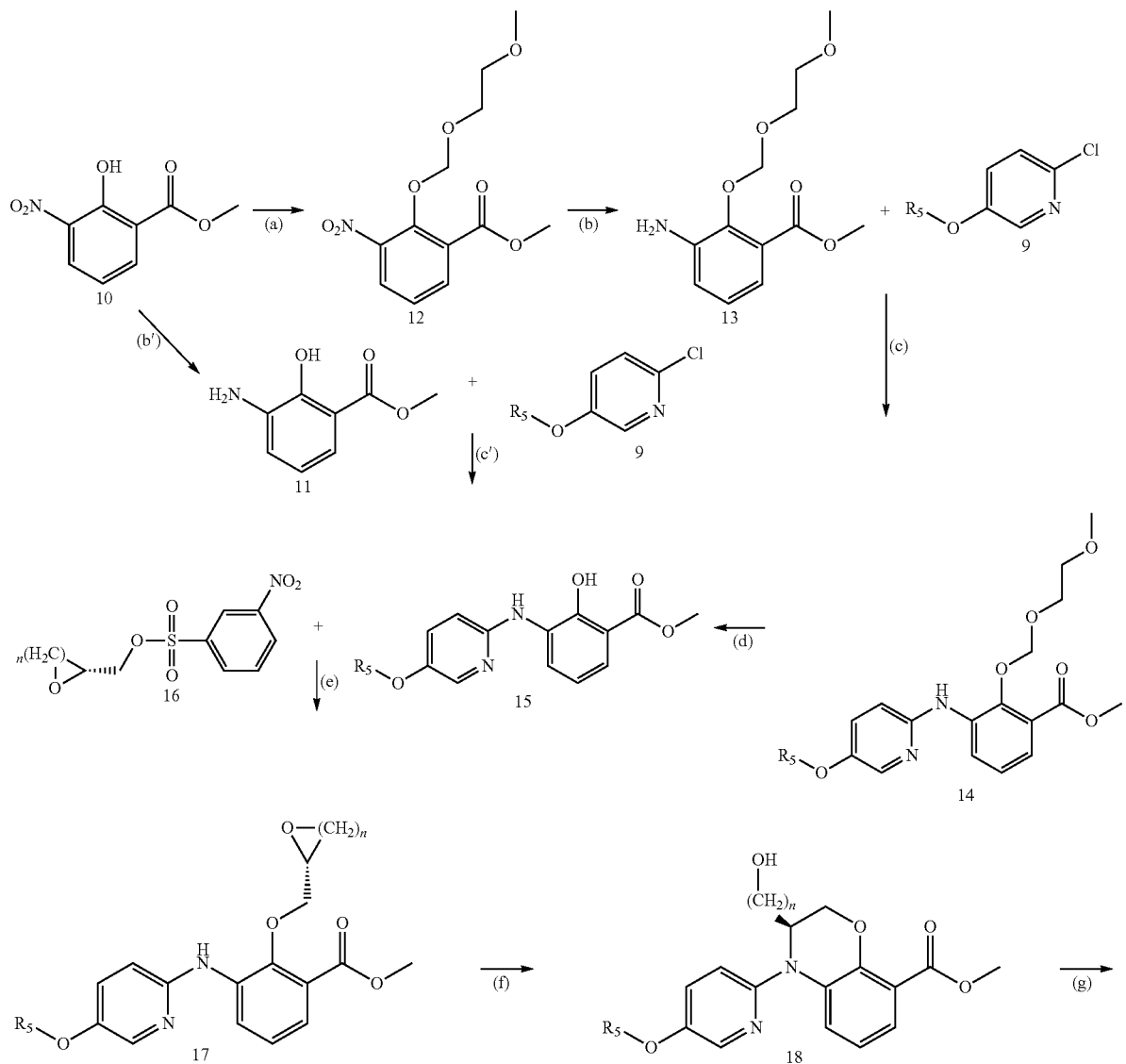

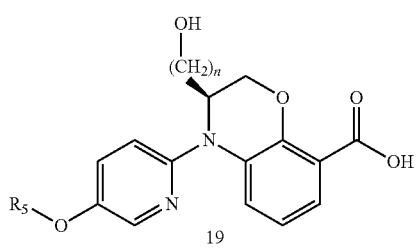

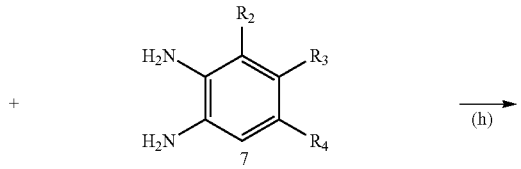

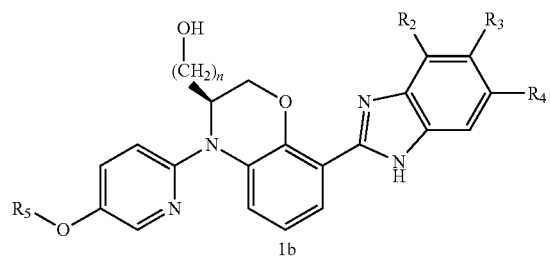

wherein, $R_2$, $R_3$, $R_4$ and $R_5$ are respectively as described above, n is an integer of 1 to 3.

In step (a), as seen in Reaction Scheme 2, compound 10 is allowed to react in an organic solvent in the presence of chloromethoxyethoxymethane under basic conditions to afford compound 12. In detail, the step may be conducted at room temperature for 2 hrs in dimethylformamide as a solvent with $K_2CO_3$ serving as a base.

In steps (b) and (b'), compounds 10 and 12 are reduced into compounds 11 and 13, respectively, in a process similar to that of step 2) of Reaction Scheme 1.

In steps (c) and (c'), compounds 11 and 13 are reacted with compound 9 in the presence of a catalyst and a ligand in an organic solvent under basic conditions to synthesize compounds 14 and 15, respectively. For use in this reaction, $Pd(OAc)_2$ may be properly suggested as the catalyst, 2,2'-bis (diphenylphosphino)-1,1'-binaphthyl as the ligand, $Cs_2CO_3$ as the base and toluene or 1,4-dioxane as the organic solvent. Each of compounds 11 and 13 may be used in an amount of from 1 to 1.2 moles per mole of compound 9. This reaction may be conducted at 90 to 110° C. for 12 to 18 hrs.

In step (d), compound 14 is hydrolyzed into compound 15 in the presence of HCl in an organic solvent. This hydrolysis may be conducted at room temperature for 24 hrs and methanol may be used as the solvent.

Turning to step (e), compound 15 is reacted with compound 16 in an organic solvent under basic conditions to afford compound 17. Compound 16 may be obtained by chemical synthesis or a commercial variant may be used. It may be used in an amount of from 1 to 1.2 moles per mole of compound 15. This reaction may be conducted at room temperature for 12 to 16 hrs in dimethylformamide as a solvent while $K_2CO_3$ is used as a base.

In step (f), compound 17 is allowed to undergo an intramolecular reaction at 100° C. for 2 to 5 hours in an organic solvent under basic conditions to afford compound 18. For use in this reaction, $K_2CO_3$ may be properly suggested as the base and dimethylformamide as the organic solvent.

In step (g), compound 18 is hydrolyzed at 60° C. for 3 hours into compound 19 in the presence of sodium hydroxide in an organic solvent. Methanol may be a suitable solvent.

Finally in step (h), compound 19 is condensed with compound 7 in the same manner as in step 5) of Reaction Scheme 1 to give an amide compound which is then cyclized into compound 1b.

Exhibiting excellent inhibitory activity against vanilloid receptor-1 without inducing a change in body temperature, the compounds of Chemical Formula 1 in accordance with the present invention can be useful for preventing or treating a disease associated with antagonistic activity of vanilloid receptor-1.

The following examples are set forth to illustrate and provide a better understanding of the present invention but are not to be construed as limiting the present invention.

Example 1

Preparation of 8-(6-tert-Butyl-1H-benzo[d]imidazol-2-yl)-4-(5-methoxypyridin-2-yl)-3,4-dihydro-2H-benzo[b][1,4]oxazine (Step 1) Preparation of 2-hydroxy-3-nitrobenzoic acid ethyl ester To a solution of 2-hydroxy-3-nitrobenzoic acid 10.0 g (55 mmol) in ethanol 100 mL was added dropwise 2 mL of conc. HCl, followed by stirring for 24 hrs under reflux. The mixture was cooled to room temperature, concentrated in a vacuum, and diluted with ethyl acetate. This dilution was washed with an aqueous saturated sodium bicarbonate solution and an aqueous saturated NaCl solution, dried over magnesium sulfate and concentrated in a vacuum. The concentrate was purified using column chromatography (developing solvent: ethylacetate/hexane=1/4) to afford the title compound 10.0 g (yield 86%).

(Step 2) Preparation of 3-amino-2-hydroxybenzoic acid ethyl ester

To a solution of 2-hydroxy-3-nitrobenzoic acid ethyl ester 8.4 g (40 mmol) of step 1 in methanol 100 mL was added 5% Pd/C 0.84 g, after which the reactor was filled hydrogen gas, followed by stirring at room temperature for 5 hrs. Ammoniumformate 0.5 g was added to the reaction mixture before re-filling with hydrogen gas and re-stirring at room temperature for 24 hrs. The catalyst was removed by celite filtration, followed by vacuum concentration to afford the title compound 7.2 g (yield 99%).

(Step 3) Preparation of 3,4-dihydro-2H-benzo[b][1,4]oxazine-8-carboxylic acid ethyl ester To a solution of ethyl ester 3.6 g (20 mmol) of step 2 in dimethylformamide 30 mL was added K₂CO₃ 5.5 g (40 mmol), followed by stirring at room temperature for 10 min. Dibromoethane 1.9 mL (22 mmol) was added dropwise to the reaction mixture which was then stirred for 3 hours under reflux. The reaction mixture was cooled to room temperature, concentrated in a vacuum, diluted with ethylacetate, and washed with a saturated sodium bicarbonate solution and a saturated NaCl solution. The resulting residue was dried over magnesium sulfate and concentrated in a vacuum to afford 3.7 g of the title compound (yield 89%).

(Step 4) Preparation of 3,4-dihydro-2H-benzo[b][1,4]oxazine-8-carboxylic acid

To a solution of 3,4-dihydro-2H-benzo[b][1,4]oxazine-8-carboxylic acid ethyl ester 2.1 g (10 mmol) of step 3 in a mixture of tetrahydrofuran 10 mL and distilled water 10 mL was added lithium hydroxide monohydrate 0.85 g (20 mmol), followed by stirring at room temperature for 8 hrs. After concentrating the reaction mixture in a vacuum, the reaction mixture was diluted with ethylacetate, washed with 1N HCl and a saturated NaCl solution, and dried over magnesium sulfate. The residue was concentrated in a vacuum and crystallized in ethylacetate/hexane to obtain 1.6 g of the title compound (yield 89%).

(Step 5) Preparation of 4-(5-tert-butyl-1H-benzo[d]imidazol-2-yl)benzene amine

To a solution of 3,4-dihydro-2H-benzo[b][1,4]oxazine-8-carboxylic acid 3.6 g (20 mmol) of step 4 in dimethylformamide 50 mL were added 4-tert-butylbenzen-1,2-diamine 3.3 g (20 mmol), diisopropylethylamine 7 mL (40 mmol) and O-(7-azabenzotriazol-1-yl)-N,N,N',N'-tetramethyluronium hexafluorophosphate 11 g (30 mmol), followed by stirring at room temperature for 3 hrs. The reaction mixture was diluted with ethylacetate, washed with a saturated sodium bicarbonate solution and a saturated NaCl solution, and dried over magnesium sulfate before being concentrated in a vacuum. The residue thus obtained was dissolved in acetic acid/toluene (45 mL/5 mL), stirred at 70° C. for 4 hrs, cooled to room temperature, and concentrated in a vacuum. The concentrate was dissolved in ethylacetate, washed with a saturated sodium bicarbonate solution and a saturated NaCl solution, and dried over magnesium sulfate before vacuum concentration. Purification by column chromatography (developing solvent: ethylacetate/hexane=1/1) gave 5.2 g of the title compound (yield 85%).

(Step 6) Preparation of 8-(6-tert-butyl-1H-benzo[d]imidazol-2-yl)-4-(5-methoxypyridin-2-yl)-3,4-dihydro-2H-benzo[b][1,4-]oxazine To a solution of 4-(5-tert-butyl-1H-benzo[d]imidazol-2-yl)benzene amine 3.1 g (10 mmol) in toluene 10 mL were added 2-chloro-5-methoxy pyridine 1.5 g (10 mmol), Pd(OAc)₂ 0.1 g (0.5 mmol) and 2,2'-bis(diphenylphosphino)-1,1'-binaphthyl 0.5 g (0.8 mmol) and Cs₂CO₃ 4.6 g (14 mmol), followed by stirring at 90° C. for 12 hrs. The reaction mixture was cooled to room temperature, concentrated under reduced pressure, and diluted with ethylacetate. The product thus formed was washed with a saturated sodium bicarbonate solution and a saturated NaCl solution, dried over magnesium sulfate and concentrated in a vacuum. The residue was purified by column chromatography (developing solvent: ethylacetate/hexane=2/3) to give 3.5 g of the title compound (yield 85%).

¹H NMR (MeOD-d4) δ: 8.04 (d, 1H, J=3.0 Hz), 7.79 (dd, 2H, J=7.8, 1.5 Hz), 7.67 (d, 1H, J=1.7 Hz), 7.56 (d, 1H, J=8.6 Hz), 7.38 (m, 2H), 7.25 (d, 1H, J=9.0 Hz), 7.17 (dd, 1H, J=8.1, 1.4 Hz), 6.95 (t, 1H, J=8.0 Hz), 4.52 (t, 2H, J=4.4 Hz), 3.99 (t, 2H, J=4.4 Hz), 3.86 (s, 3H), 1.41 (s, 9H)

Example 2

Preparation of (S)-(4-(5-methoxypyridin-2-yl)-8-(6-(trifluoromethyl)-1H-benzo[d]imidazol-2-yl)-3,4-dihydro-2H-benzo[b][1,4]oxazin-3-yl)methanol (Step 1) Preparation of 2-((2-methoxyethoxy)methoxy)-3-nitrobenzoic acid methyl ester To a solution of 2-hydroxy-3-nitrobenzoic acid methyl ester 9.9 g (50 mmol) in dimethylformamide 100 mL were added K₂CO₃ 7.6 g (55 mmol) and chloromethoxyethoxymethane 6.3 mL (55 mmol), followed by stirring at room temperature for 2 hrs. The resulting reaction mixture was concentrated in a vacuum, diluted with ethylacetate and washed with distilled water and a saturated NaCl solution. The residue was dried over magnesium sulfate and concentrated under reduced pressure to give the title compound 14.0 g (yield 98%).

(Step 2) Preparation of 3-amino-2-((2-methoxyethoxy)methoxy)benzoic acid methyl ester To a solution of 2-((2-methoxyethoxy)methoxy)-3-nitrobenzoic acid methyl ester 5.0 g (17.5 mmol) of step 1 in methanol 50 mL was added 5% Pd/C 0.5 g, and the reactor was filled with hydrogen gas, after which the reaction mixture was stirred at room temperature for 24 hrs. The catalyst was removed off by celite filtration before concentrating the reaction mixture in a vacuum. Purification by column chromatography (developing solvent: ethylacetate/hexane=1/1) afforded 4.2 g of the title compound (yield 95%).

(Step 3) Preparation of methyl 2-[(2-methoxyethoxy)methoxy]-3-(5-methoxypyridin-2-ylamino)benzoate To a solution of 3-amino-2-((2-methoxyethoxy)methoxy) benzoic acid methyl ester 1.25 g (4.9 mmol) of step 2 in 1,4-dioxane 10 mL were added 2-chloro-5-methoxypyridine 0.70 g (4.9 mmol), Pd(OAc)₂ 0.11 g (0.49 mmol), 2,2'-bis(diphenylphosphino)-1,1'-binaphthyl 0.31 g (0.49 mmol) and Cs₂CO₃ 3.85 g (9.8 mmol), followed by stirring at 90° C. for 12 hrs. The reaction mixture was cooled to room temperature, concentrated under reduced pressure, diluted with ethylacetate, and washed with a saturated sodium bicarbonate solution and a saturated NaCl solution. After drying over magnesium sulfate and concentration in a vacuum, purification by column chromatography (developing solvent: ethylacetate/hexane=1/2) afforded 1.2 g of the title compound (yield 68%).

(Step 4) Preparation of methyl-2-hydroxy-3-(5-methoxypyridin-2-ylamino)benzoate

To a solution of methyl 2-[(2-methoxyethoxy)methoxy]-3-(5-methoxypyridin-2-ylamino)benzoate 1.0 g (2.8 mmol)

of step 3 in methanol 20 mL was added 6NHCl 2 mL, followed by stirring at 40° C. for 30 min. The reaction mixture was cooled to room temperature, concentrated in a vacuum, diluted with ethylacetate, washed with distilled water, and a saturated NaCl solution. After drying over magnesium sulfate and concentration in a vacuum, purification by column chromatography (developing solvent: ethylacetate/hexane=1/2) afforded 0.70 g of the title compound (yield 90%).

(Step 5) Preparation of (R)-methyl-3-(5-methoxypyridin-2-ylamino)-2-(oxirane-2-ylmethoxy)benzoate To a solution of methyl-2-hydroxy-3-(5-methoxypyridin-2-ylamino)benzoate 0.91 g (3.3 mmol) of step 4 in dimethylformamide 10 mL were (R)-glycidyl nosylate 1.0 g (4 mmol) and $K_2CO_3$ 0.5 g (3.6 mmol), followed by stirring at room temperature for 12 hrs. The reaction mixture was concentrated in a vacuum, diluted with ethylacetate, and washed with distilled water and a saturated NaCl solution. After drying over magnesium sulfate and vacuum concentration, purification by column chromatography (developing solvent: ethylacetate/hexane=1/2) afforded 0.95 g of the title compound (yield 87%).

(Step 6) Preparation of (S)-methyl-3-(hydroxymethyl)-4-(5-methoxypyridin-2-yl)-3,4-dihydro-2H-benzo[b][1,4]oxazine-8-carboxylate To a solution of (R)-methyl-3-(5-methoxypyridin-2-ylamino)-2-(oxiran-2-ylmethoxy)benzoate 0.53 g (1.6 mmol) of step 5 in dimethylformamide 5 mL was added $K_2CO_3$ 0.28 g (2.0 mmol), followed by stirring at 100° C. for 5 hrs. The reaction mixture is cooled to room temperature, concentrated in a vacuum, diluted with ethylacetate, and washed with distilled water and a saturated NaCl solution. After drying over magnesium sulfate and concentration in a vacuum, purification by column chromatography (developing solvent: ethylacetate/hexane=1/1) afforded 0.50 g of the title compound (yield 94%).

(Step 7) Preparation of (S)-3-(hydroxymethyl)-4-(5-methoxypyridin-2-yl)-3,4-dihydro-2H-benzo[b][1,4]oxazine-8-carboxylic acid To a solution of (S)-methyl-3-(hydroxymethyl)-4-(5-methoxypyridin-2-yl)-3,4-dihydro-2H-benzo[b][1,4]oxazine-8-carboxylate 3.6 g (11 mmol) of step 6 in methanol 40 mL was dropwise added 10 mL of 4N NaCl. The reaction mixture was refluxed at 60° C. for 3 hrs with stirring and then cooled to room temperature. Neutralization with 1N HCl 40 mL yielded the title compound as a precipitate. This was filtered, washed with distilled water and concentrated in a vacuum. Product: 2.6 g (yield 75%).

(Step 8) Preparation of (S)-(4-(5-methoxypyridin-2-yl)-8-(6-(trifluoromethyl)-1H-benzo[d]imidazol-2-yl)-3,4-dihydro-2H-benzo[b][1,4]oxazin-3-yl)methanol To a solution of (S)-3-(hydroxymethyl)-4-(5-methoxypyridin-2-yl)-3,4-dihydro-2H-benzo[b][1,4]oxazine-8-carboxylic acid 3.2 g (10 mmol) of step 7 in dimethylformamide 50 mL were 4-(trifluoromethyl)benzen-1,2-diamine 1.9 g (11 mmol), diisopropylethylamine 3.5 mL (20 mmol) and O-(7-azabenzotriazol-1-yl)-N,N,N',N'-tetramethyluronium hexafluorophosphate 5.7 g (15 mmol), followed by stirring at room temperature for 3 hrs. The reaction mixture was diluted with ethylacetate, washed with a saturated sodium bicarbonate solution and a saturated NaCl solution, dried over magnesium sulfate and concentrated in a vacuum. The concentrate was dissolved in acetic acid/toluene (90 mL/10 mL), heated at 75° C. for 4 hrs with stirring, cooled to room temperature and concentrated in a vacuum. The concentrate was dissolved in ethylacetate, washed with a saturated sodium bicarbonate solution and a saturated NaCl solution, dried over magnesium sulfate, and concentrated under reduced pressure. Purification by column chromatography (developing solvent: ethylacetate/hexane=2/3) afforded 4.1 g of the title compound (yield 82%).

$^1$H NMR (MeOD-d4) δ: 8.05 (d, 1H, J=2.8 Hz), 7.95 (s, 1H), 7.79 (dd, 2H, J=7.7, 1.5 Hz), 7.54 (d, 1H, J=8.4 Hz), 7.40 (dd, 1H, J=8.9, 3.0 Hz), 7.34 (d, 1H, J=8.9 Hz), 7.17 (dd, 1H, J=8.1, 1.4 Hz), 6.97 (t, 1H, J=8.0 Hz), 4.85 (d, 1H, J=10.9 Hz), 4.31 (m, 1H), 4.26 (dd, 1H, J=10.9, 2.6 Hz), 3.89-3.84 (m, 4H), 3.68 (dd, 1H, J=10.9, 8.0 Hz)

Example 3

Preparation of (S)-(8-(5,6-dichloro-1H-benzo[d]imidazol-2-yl)-4-(5-methoxypyridin-2-yl)-3,4-dihydro-2H-benzo[B][1,4]oxazin-3-yl)methanol The same procedure as in step 8 of Example 2 was repeated, with the exception of using 4,5-dichlorobenzen-1,2-diamine instead of 4-(trifluoromethyl)benzen-1,2-diamine, to prepare 4.0 g of the title compound (yield 87%).

$^1$H NMR (MeOD-d4) δ: 8.05 (d, 1H, J=2.8 Hz), 7.77 (m, 3H), 7.41 (dd, 1H, J=9.0, 2.9 Hz), 7.34 (d, 1H, J=8.9 Hz), 7.16 (dd, 1H, J=8.1, 1.3 Hz), 6.96 (t, 1H, J=7.9 Hz), 4.84 (d, 1H, J=10.9 Hz), 4.31 (m, 1H), 4.26 (dd, 1H, J=10.8, 2.5 Hz), 3.88-3.80 (m, 4H), 3.67 (dd, 1H, J=10.9, 8.0 Hz)

Example 4

Preparation of (S)-(4-(5-methoxypyridin-2-yl)-8-(6-(trifluoromethoxy)-1H-benzo[d]imidazol-2-yl)-3,4-dihydro-2H-benzo[b][1,4]oxazin-3-yl)methanol The same procedure as in step 8 of Example 2 was repeated, with the exception of using 4-(trifluoromethoxy)benzen-1,2-diamine instead of 4-(trifluoromethyl)benzen-1,2-diamine, to prepare 4.3 g of the title compound (yield 91%).

$^1$H NMR (MeOD-d4) δ: 8.06 (d, 1H, J=2.9 Hz), 7.77 (dd, 1H, J=7.8, 1.5 Hz), 7.69 (d, 1H, J=8.8 Hz), 7.55 (s, 1H), 7.42 (dd, 1H, J=9.0, 3.0 Hz), 7.17 (m, 2H), 6.97 (t, 1H, J=8.0 Hz), 4.84 (dd, 1H, J=10.9, 1.4 Hz), 4.31 (m, 1H), 4.26 (dd, 1H, J=10.9, 2.6 Hz), 3.90-3.84 (m, 4H), 3.68 (dd, 1H, J=10.9, 8.1 Hz)

Example 5

Preparation of (S)-(8-(4-bromo-6-(trifluoromethoxy)-1H-benzo[d]imidazol-2-yl)-4-(5-methoxypyridin-2-yl)-3,4-dihydro-2H-benzo[B][1,4]oxazin-3-yl)methanol The same procedure as in step 8 of Example 2 was repeated, with the exception of using 3-bromo-5-(trifluoromethoxy)benzen-1,2-diamine instead of 4-(trifluoromethyl)benzen-1,2-diamine, to prepare 5.2 g of the title compound (yield 94%).

$^1$H NMR (MeOD-d4) δ: 8.05 (d, 1H, J=2.8 Hz), 7.86 (brs, 1H), 7.55 (s, 1H), 7.42 (dd, 2H, J=9.0, 2.9 Hz), 7.34 (d, 1H, J=8.9 Hz), 7.18 (dd, 1H, J=8.1, 1.4 Hz), 6.97 (t, 1H, J=8.0

Hz), 4.82 (d, 1H, J=10.7 Hz), 4.34 (m, 1H), 4.26 (dd, 1H, J=10.9, 2.6 Hz), 3.93-3.84 (m, 4H), 3.68 (dd, 1H, J=10.9, 8.0 Hz)

Example 6

Preparation of (S)-(8-(6-chloro-5-fluoro-1H-benzo[d]imidazol-2-yl)-4-(5-methoxypyridin-2-yl)-3,4-dihydro-2H-benzo[b][1,4]oxazin-3-yl)methanol The same procedure as in step 8 of Example 2 was repeated, with the exception of using 4-chloro-5-fluorobenzen-1,2-diamine instead of 4-(trifluoromethyl)benzen-1,2-diamine, to prepare 3.9 g of the title compound (yield 88%).
¹H NMR (MeOD-d4) δ: 8.06 (d, 1H, J=2.9 Hz), 7.75 (dd, 1H, J=7.8, 1.4 Hz), 7.70 (d, 1H, J=6.7 Hz), 7.47 (d, 1H, J=9.4 Hz), 7.42 (dd, 1H, J=9.0, 3.0 Hz), 7.35 (d, 1H, J=8.9 Hz), 7.16 (dd, 1H, J=8.1, 1.5 Hz), 6.96 (t, 1H, J=8.0 Hz), 4.84 (dd, 1H, J=10.9, 1.4 Hz), 4.31 (m, 1H), 4.26 (dd, 1H, J=10.9, 2.6 Hz), 3.90-3.84 (m, 4H), 3.68 (dd, 1H, J=10.9, 8.1 Hz)

Example 7

Preparation of (S)-(8-(4-bromo-6-(trifluoromethyl)-1H-benzo[d]imidazol-2-yl)-4-(5-methoxypyridin-2-yl)-3,4-dihydro-2H-benzo[b][1,4]oxazin-3-yl)methanol The same procedure as in step 8 of Example 2 was repeated, with the exception of using 3-bromo-5-(trifluoromethyl)benzen-1,2-diamine instead of 4-(trifluoromethyl)benzen-1,2-diamine, to prepare the title compound 4.0 g (yield 75%).
¹H NMR (MeOD-d4) δ: 8.05 (d, 1H, J=2.8 Hz), 7.93 (s, 1H), 7.71 (s, 1H), 7.42 (dd, 2H, J=9.0, 2.9 Hz), 7.34 (d, 1H, J=8.9 Hz), 7.18 (dd, 1H, J=8.1, 1.4 Hz), 6.97 (t, 1H, J=8.0 Hz), 4.82 (d, 1H, J=10.7 Hz), 4.34 (m, 1H), 4.26 (dd, 1H, J=10.9, 2.6 Hz), 3.93-3.84 (m, 4H), 3.68 (dd, 1H, J=10.9, 8.0 Hz)

Example 8

Preparation of (S)-(8-(4-chloro-6-(trifluoromethyl)-1H-benzo[d]imidazol-2-yl)-4-(5-methoxypyridin-2-yl)-3,4-dihydro-2H-benzo[b][1,4]oxazin-3-yl)methanol The same procedure as in step 8 of Example 2 was repeated, with the exception of using 3-chloro-5-(trifluoromethyl)benzen-1,2-diamine instead of 4-(trifluoromethyl)benzen-1,2-diamine, to prepare the title compound 4.3 g (yield 88%).
¹H NMR (MeOD-d4) δ: 8.05 (d, 1H, J=2.8 Hz), 7.90 (s, 2H), 7.67 (m, 1H), 7.42 (dd, 1H, J=9.0, 2.9 Hz), 7.34 (d, 1H, J=8.9 Hz), 7.18 (dd, 1H, J=8.1, 1.4 Hz), 6.97 (t, 1H, J=8.0 Hz), 4.82 (d, 1H, J=10.7 Hz), 4.34 (m, 1H), 4.26 (dd, 1H, J=10.9, 2.6 Hz), 3.93-3.84 (m, 4H), 3.68 (dd, 1H, J=10.9, 8.0 Hz)

Example 9

Preparation of (S)-(8-(4,6-dibromo-1H-benzo[d]imidazol-2-yl)-4-(5-methoxypyridin-2-yl)-3,4-dihydro-2H-benzo[b][1,4]oxazin-3-yl)methanol The same procedure as in step 8 of Example 2 was repeated, with the exception of using 3,5-dibromobenzen-1,2-diamine instead of 4-(trifluoromethyl)benzen-1,2-diamine, to prepare the title compound 4.6 g (yield 84%).
¹H NMR (MeOD-d4) δ: 8.05 (d, 1H, J=2.8 Hz), 7.80 (m, 2H), 7.58 (m, 1H), 7.42 (dd, 1H, J=9.0, 2.9 Hz), 7.34 (d, 1H, J=8.9 Hz), 7.18 (dd, 1H, J=8.1, 1.4 Hz), 6.97 (t, 1H, J=8.0 Hz), 4.82 (d, 1H, J=10.7 Hz), 4.34 (m, 1H), 4.26 (dd, 1H, J=10.9, 2.6 Hz), 3.93-3.84 (m, 4H), 3.68 (dd, 1H, J=10.9, 8.0 Hz)

Experimental Example 1

Inhibitory Effect on Calcium Influx Via a Vanilloid Receptor

In order to confirm the antagonistic activities of the inventive compounds, inhibitory effects of the compounds on calcium influx were examined as follows.
1) Cell Culture
hVR-1-HEK293 cell line is a human embryonic kidney (HEK) cell 293 Tet-on strain transformed with a human vanilloid-1 gene (pTRE2hyg-hVR-1 7.8 kb). The cell line can modulate the expression of TRPV1, depending on whether doxycycline, a derivative of tetracycline, is present or not.

In order to elucidate the inhibitory effect on calcium influx, the expression of TRPV1 was induced by culturing hVR-1-HEK293 cell line in a medium containing doxycycline for 2 days.

Specifically, hVR-1-HEK293 cells were cultured in a T75 flask to about 80% confluency, separated from the flask by treating with trypsin solution, and then collected by centrifugation. The cells were suspended in a medium containing 1 μg/mL of doxycycline, and the resulting suspension was diluted to a concentration of 2~4×10⁵ cells/mL. 100 μL of the cell suspension was placed in each well of a 96-well black plate. The cells were cultured in 5% $CO_2$ incubator at 37° C. for 2 days, and used for the following procedure.
2) Preparation of Compound Samples The compounds, prepared in the Examples 1 to 9 of the present invention, were dissolved in dimethyl sulfoxide (DMSO) to obtain compound samples.
3) Measurement of Calcium Influx The cells prepared in 1) above were cultured at 37° C. for 90 min in a solution containing Fluo-3/AM, a fluorescent dye, as a calcium indicator so that the fluorescent dye was permeated into the cells. Then the cells were washed three times with D-PBS (Dulbecco's phosphate buffered saline) containing 10 mM HEPES (4-(2-hydroxyethyl)-1-piperazine ethanesulfonic acid) to remove the residual fluorescent dye. 193 μL of D-PBS was added to each well, followed by addition of various concentrations (0.015~2000 nM) of the compounds. In order to stimulate calcium influx through a vanilloid receptor, the cells were treated with 1 μM of capsaicin. The inhibitory effect of various concentrations (0.015~2000 nM) of compounds on intracellular calcium influx was measured by using a fluorimeter. Equivalent amounts of (R)-1-(2-bromophenyl)-3-(1-(5-(trifluoromethyl)pyridin-2-yl)pyrrolidin-3-yl)urea (also, referred to SB-705498) was used as a control group. The obtained data were input to the Hill equation represented by the following formula I and the values were analyzed:

Intracellular calcium influx=(florescent intensity of experimental group−florescent intensity of background)/(florescent intensity of positive control−florescent intensity of background)×100    [Formula 1]

The inhibitory activities were evaluated from the obtained intracellular calcium influx values according to the following criteria. The results are shown in the following Table 1.

−: $IC_{50}>1000$ nM; +: $IC_{50}=501{\sim}1000$ nM; ++: $IC_{50}=101{\sim}500$ nM; +++: $IC_{50}=20{\sim}100$ nM; ++++: $IC_{50}<20$ nM

TABLE 1

| Example | I.A.* | Example | I.A. |
|---|---|---|---|
| 1 | ++ | 2 | +++ |
| 3 | +++ | 4 | +++ |
| 5 | ++++ | 6 | +++ |
| 7 | ++ | 8 | +++ |
| 9 | ++ | | |

*I. A.: inhibitory activity

As shown in Table 1, the compounds of the present invention showed $IC_{50}$ ranging from 10 nM to 100 nM. In contrast, the control group administered with SB-705498 showed $IC_{50}$ ranging from 100 nM to 150 nM. These results demonstrate that the compounds of the present invention have excellent inhibitory activities on the calcium influx.

Experimental Example 2

Effect on Pain

In order to evaluate the effect on pain of the compounds prepared in the Examples 1 to 9, behaviors such as twisting or writhing of body resulted from pain were verified by the phenyl-p-quinone (PBQ)-induced writhing experiment using mice.

5 week-old ICR male mice were used as experimental animals and PBQ (0.02%), as a chemical stimulator. The suspensions of 20 mg of the compounds of the present invention and an excipient such as Na-CMC (sodium carboxymethyl cellulose) in 10 mL of saline were used as test compounds. The test compounds were orally administered to the mice and after 1 hour, PBQ was intraperitoneally administrated in an amount of 10 mL per kg of body weight. The writhing number of each mouse was measured for 10 min starting from 5 min after the administration, and the analgesic effect was verified by counting the reduced number compared to the control group administered with only excipient and calculating the % inhibitory rate according to the following Formula 2. Also, equivalent amounts of SB-705498 were administered as a reference compound for the comparison of the effect on pain between SB-705498 and the compounds of the present invention.

% inhibition rate=(writhing # of control group−writhing # of test group)/writhing # of control group× 100    [Formula 2]

The inhibitory activity was evaluated from the obtained % inhibition rate, according to the following parameters.
+: <20%; ++: 20~50%; +++: 51-80%; ++++: >80%

TABLE 2

| Example | I.A.* | Example | I.A. |
|---|---|---|---|
| 1 | ++ | 2 | ++ |
| 3 | ++ | 4 | ++ |
| 5 | +++ | 6 | +++ |
| 7 | ++ | 8 | +++ |
| 9 | ++ | | |

*I. A.: inhibitory activity

As can be seen from Table 2, most compounds of the present invention showed inhibition rates ranging from 30% to 80%. In contrast, the reference compound group showed <20% (+). These results demonstrate that the compounds of the present invention have excellent analgesic activities.

Experimental Example 3

Assay for Body Temperature Change

With the knowledge that some TRPV1 antagonists show the side effect of increasing the body temperature (Gavva et al., 2008, Pain, 136, 202-210), changes in body temperature associated with the compounds prepared in the Examples of the present invention were assessed.

7-week-old SD rats (Sprague-Dawley rats) were employed for this evaluation. Each of the compounds of the Examples was orally administered once at a dose of 10 ml/kg by compulsion. Before administration, the compounds were suspended, together with the excipient Na-CMC (sodium carboxymethyl cellulose), in saline 10 mL. Rectal temperatures of the rats were measured 1 hr and immediately (0 hr) prior to administration, and at the 30 min, 1 hr, 2 hr, 4 hr, 6 hr and 8 hr marks after administration using a thermometer (Shibaura Electronic Corporation, TD-300). The data were expressed as mean values ±S.E.M. Statistical data was analyzed by one way ANOVA, and statistical significance was analyzed in comparison with the excipient-treated control using Dunnett's t-test. The results are summarized in Table 3, below. Meanwhile, N-(4-(6-(4-(trifluoromethyl)phenyl)pyridin-4-yloxy)benzo[d]thiazol-2-yl)acetamide (hereinafter referred to as "AMG-517") was used at a dose of 3 mg/kg, as a positive control.

TABLE 3

| Example | Change in Body Temp. | Example | Change in Body Temp. |
|---|---|---|---|
| 1 | +/− | 2 | + |
| 3 | +/− | 4 | +/− |
| 5 | + | 6 | +/− |
| 7 | + | 8 | +/− |
| 9 | + | | |

Evaluation was conducted according to the following parameters:
+/−: ±<0.5° C.
+: 0.5~1.0° C.
++: 1.1~1.5° C.
+++: >1.5° C.

When administered in pharmaceutically effective amounts, as is apparent from the data of Table 3, the compounds according to the present invention do not cause a change in body temperature. In contrast, the positive control which was administered AMG-517 at a dose of 3 mg/kg which was even lower than that of the compounds of the present invention, was found to increase the body temperature by 1.06° C. These data demonstrate that the compounds according to the present invention are safe to the body.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

What is claimed is:

1. A compound, represented by the following Chemical Formula 1, or a pharmaceutically acceptable salt thereof:

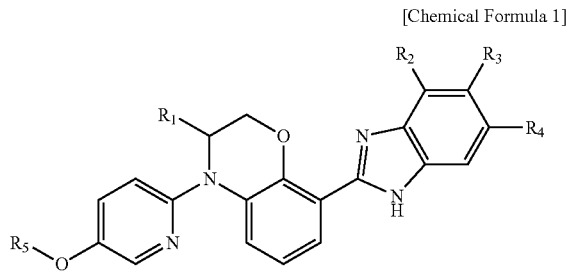

[Chemical Formula 1]

wherein,
R$_1$ is hydrogen or C$_{1-3}$ hydroxyalkyl;
R$_2$ is hydrogen or halogen;
R$_3$ is hydrogen or halogen;
R$_4$ is hydrogen, halogen, C$_{1-4}$ alkyl, C$_{1-3}$ haloalkyl or C$_{1-3}$ haloalkoxy; and
R$_5$ is C$_{1-4}$ alkyl.

2. The compound or pharmaceutically acceptable salt according to claim 1, wherein R$_1$ is hydrogen or hydroxymethyl.

3. The compound or pharmaceutically acceptable salt according to claim 1, wherein:
R$_2$ and R$_3$ are each hydrogen; and
R$_4$ is C$_{1-4}$ alkyl or C$_{1-3}$ haloalkoxy.

4. The compound or pharmaceutically acceptable salt according to claim 1, wherein:
R$_2$ is hydrogen; and
R$_3$ and R$_4$ are each halogen.

5. The compound or pharmaceutically acceptable salt according to claim 1, wherein:
R$_2$ is halogen,
R$_3$ is hydrogen, and
R$_4$ is halogen, C$_{1-3}$ haloalkyl or C$_{1-3}$ haloalkoxy.

6. The compound or pharmaceutically acceptable salt according to claim 1, wherein R$_2$ is hydrogen, Br or Cl.

7. The compound or pharmaceutically acceptable salt according to claim 1, wherein R$_3$ is hydrogen, F or Cl.

8. The compound or pharmaceutically acceptable salt according to claim 1, wherein R$_4$ is Br, Cl, C(CH$_3$)$_3$, CF$_3$ or OCF$_3$.

9. The compound or pharmaceutically acceptable salt according to claim 1, wherein R$_5$ is methyl.

10. The compound according to claim 1, or the pharmaceutically acceptable salt thereof, which is selected from the group consisting of:
1) 8-(6-tert-butyl-1H-benzo[d]imidazol-2-yl)-4-(5-methoxypyridin-2-yl)-3,4-dihydro-2H-benzo[b][1,4]oxazine,
2) (S)-(4-(5-methoxypyridin-2-yl)-8-(6-(trifluoromethyl)-1H-benzo[d]imidazol-2-yl)-3,4-dihydro-2H-benzo[b][1,4]oxazin-3-yl)methanol,
3) (S)-(8-(5,6-dichloro-1H-benzo[d]imidazol-2-yl)-4-(5-methoxypyridin-2-yl)-3,4-dihydro-2H-benzo[b][1,4]oxazin-3-yl)methanol,
4) (S)-(4-(5-methoxypyridin-2-yl)-8-(6-(trifluoromethoxy)-1H-benzo[d]imidazol-2-yl)-3,4-dihydro-2H-benzo[b][1,4]oxazin-3-yl)methanol,
5) (S)-(8-(4-bromo-6-(trifluoromethoxy)-1H-benzo[d]imidazol-2-yl)-4-(5-methoxypyridin-2-yl)-3,4-dihydro-2H-benzo[b][1,4]oxazin-3-yl)methanol,
6) (S)-(8-(6-chloro-5-fluoro-1H-benzo[d]imidazol-2-yl)-4-(5-methoxypyridin-2-yl)-3,4-dihydro-2H-benzo[b][1,4]oxazin-3-yl)methanol,
7) (S)-(8-(4-bromo-6-(trifluoromethyl)-1H-benzo[d]imidazol-2-yl)-4-(5-methoxypyridin-2-yl)-3,4-dihydro-2H-benzo[b][1,4]oxazin-3-yl)methanol,
8) (S)-(8-(4-chloro-6-(trifluoromethyl)-1H-benzo[d]imidazol-2-yl)-4-(5-methoxypyridin-2-yl)-3,4-dihydro-2H-benzo[b][1,4]oxazin-3-yl)methanol, and
9) (S)-(8-(4,6-dibromo-1H-benzo[d]imidazol-2-yl)-4-(5-methoxypyridin-2-yl)-3,4-dihydro-2H-benzo[b][1,4]oxazin-3-yl)methanol.

11. A pharmaceutical composition, comprising the compound or pharmaceutically acceptable salt thereof of claim 1; and a pharmaceutically acceptable carrier.

12. A method for treating a disease in a mammal, which comprises administering the compound or pharmaceutically acceptable salt thereof of any one of claims 1 to 10 to the mammal, wherein the disease is selected from the group consisting of acute pain, chronic pain, neuropathic pain, postoperative pain, migraines, arthralgia, neuropathy, nerve injury, diabetic neuropathy, neurodermatitis, bladder hypersensitivity, obesity, irritable bowel syndrome, asthma, chronic obstructive pulmonary disease, glaucoma, psoriasis, irritation of the skin, eyes or mucous membranes, reflux esophagitis, gastric-duodenal ulcers, and combinations thereof.

13. A method for treating a condition in a mammal, which comprises administering the compound or pharmaceutically acceptable salt thereof of any one of claims 1 to 10 to the mammal, wherein the condition is selected from the group consisting of cough, itching, and combinations thereof.

* * * * *

UNITED STATES PATENT AND TRADEMARK OFFICE
CERTIFICATE OF CORRECTION

PATENT NO. : 8,026,235 B1  
APPLICATION NO. : 12/909513  
DATED : September 27, 2011  
INVENTOR(S) : Ji Duck Kim et al.

It is certified that error appears in the above-identified patent and that said Letters Patent is hereby corrected as shown below:

Item (30):
"Oct. 13, 2010 (KR) ... 10-210-0099910" should read, --Oct. 13, 2010 (KR) ... 10-2010-0099910--.

Signed and Sealed this  
Twelfth Day of March, 2013

Teresa Stanek Rea  
*Acting Director of the United States Patent and Trademark Office*